(12) United States Patent
Zhang (10) Patent No.: US 8,364,248 B2
(45) Date of Patent: Jan. 29, 2013

(54) SYSTEM FOR CARDIAC PATHOLOGY DETECTION AND CHARACTERIZATION

(75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 371 days.

(21) Appl. No.: 12/830,711

(22) Filed: Jul. 6, 2010

(65) Prior Publication Data

US 2011/0054335 A1  Mar. 3, 2011

Related U.S. Application Data

(60) Provisional application No. 61/236,902, filed on Aug. 26, 2009.

(51) Int. Cl.
*A61B 5/04* (2006.01)
*G06Q 10/00* (2012.01)

(52) U.S. Cl. .............................. 600/509; 600/508; 705/2

(58) Field of Classification Search .......... 607/508–509; 705/2
See application file for complete search history.

(56) References Cited

U.S. PATENT DOCUMENTS

2009/0228298 A1* 9/2009 Xue .................................. 705/2

\* cited by examiner

*Primary Examiner* — Nicole F Lavert
(74) *Attorney, Agent, or Firm* — Alexander J Burke (57) ABSTRACT

A system improves characterization and diagnosis of cardiac electrophysiological activities by analyzing and characterizing cardiac function signals (including surface ECG signals and intra-cardiac electrograms) based on cardiac electrophysiological energy mode and pattern identification and mapping. The system accurately determines a time stamp, location and severity of cardiac pathology and clinical events by calculating a cardiac signal energy mode and energy variation and distribution. The system identifies cardiac disorders, differentiates cardiac arrhythmias, characterizes pathological severity, predicts life-threatening events, and supports evaluation of administration of drugs.

24 Claims, 8 Drawing Sheets

| Name of calculation | Calculation methods | Function & Meaning |
|---|---|---|
| 303 — Positive portion Vs. Negative portion | $\left\| \sum Energy(positive\_portion) - \sum Energy(negative\_portion) \right\|$ $\dfrac{\left\| \sum Energy(positive\_portion) - \sum Energy(negative\_portion) \right\|}{\left\| \sum Energy(positive\_portion) + \sum Energy(negative\_portion) \right\|}$ | Energy flowing, excitation conducting energy a consumpti in t cardiac tissue. |
| 305 — Depolarization portion Vs. Repolarization portion | $\sum\limits_{i \in Repolarization} E_i$ , $\sum\limits_{j \in Depolarization} E_j$ , $\dfrac{\sum\limits_{j \in Depolarization} E_j}{\sum\limits_{i \in Repolarization} E_i}$ | Energy flowing a consumpti compariso between atrial a ventricle tissue |
| 307 — Same portion in different cardiac cycle | $\sum\limits_{i \in beat\_i} E_i$ Vs. $\sum\limits_{i \in beat\_j} E_j$ , Ei, Ej ∈ $E_P, E_Q, E_R, E_S, E_{ST}$, etc. | Energy flowing a consumpti compariso between different beat. (variation) |
| 309 — different portion in same cardiac cycle | $Energy\_ratio = \dfrac{\sum\limits_{i \in ROI\_i} E_i}{\sum\limits_{i \in ROI\_j} E_j}$ , Ei, Ej ∈ $E_P, E_Q, E_R, E_S, E_{ST}$, etc. | Energy flowing a consumpti compariso in the san heart bei (variation) |

SYSTEM FOR CARDIAC PATHOLOGY DETECTION AND CHARACTERIZATION

This is a non-provisional application of provisional application Ser. No. 61/236,902 filed Aug. 26, 2009, by H. Zhang.

FIELD OF THE INVENTION

This invention concerns a system for heart performance characterization and abnormality detection by calculating a signal characteristic value based on a function of values of amplitude of an electrical signal over at least a portion of a heart beat cycle.

BACKGROUND OF THE INVENTION

Cardiac arrhythmia identification and characterization is necessary for management of cardiac disorders and irregularities. Usually, signal analysis based on electrophysiological activity (such as on ECG signals and intra-cardiac electrograms) and time domain parameters (such as magnitude and voltage) of the waveforms are utilized for cardiac arrhythmia detection and pathology diagnosis. This involves examining P wave disorders for atrial fibrillation (AF) and ST segment changes for myocardial ischemia and infarction, for example. However, known systems for cardiac arrhythmia identification and analysis based on ECG signals are subjective and need extensive expertise and clinical experience for accurate interpretation and appropriate cardiac rhythm management.

Coronary Artery Disease (CAD) and heart-related problems and cardiac arrhythmias are common and serious. Early arrhythmia recognition and characterization, such as associated with myocardial ischemia and infarction, is valuable for rhythm management of cardiac disorders and irregularities. Currently waveform morphologies and time domain parameter analysis of depolarization and repolarization, such as P wave, QRS complex, ST segment, T wave, are used for cardiac arrhythmia monitoring and identification. However, known systems based on waveform and time domain parameter analyses, are often subjective and time-consuming, and require expertise and clinical experience for accurate interpretation and proper cardiac rhythm management. Some known systems apply more sophisticated mathematical theories to biomedical signal interpretation, such as frequency analysis, symbolic complexity analysis and nonlinear entropy evaluation and focus on generating a new pathology index for qualitative cardiac arrhythmia characterization. These known systems fail to provide comprehensive cardiac electrophysiological function and activity interpretation, tissue mapping and arrhythmia localization.

Additionally, known systems typically analyze waveform characteristics (such as amplitude, latency,) or frequency domain characteristics (such as power, spectrum) which may not efficiently identify small signal changes in a partial portion (P wave, QRS complex, ST segment) of a cardiac cycle. These small changes are usually invisible in a signal wave morphology display and need extensive clinical expertise for identification. Consequently, known systems may fail to identify arrhythmia and have a high rate of false alarm indication. Known systems based on amplitude (voltage) changes and variation analysis may be inadequate to diagnose pathology and fail to accurately explain clinical information and associate signal frequency variation, for example. Known systems may fail to predict a pathological trend, especially in early stage of tissue malfunction and may not efficiently analyze and identify a real time growing trend of cardiac arrhythmias, such as a pathology trend from low risk to medium, and then to a high risk (severe and fatal) rhythm (especially for an arrhythmia such as a VT growing trend). Further, known cardiac function monitoring systems may lack sensitivity and stability for arrhythmia analysis for patient status evaluation and may generate inaccurate and unreliable data because of noise and artifacts. Environmental noise and patient movement artifacts including electrical interference, can distort a waveform and make it difficult to detect R wave and ST segment elevation accurately, and result in a false alarm. A system according to invention principles addresses these deficiencies and related problems.

SUMMARY OF THE INVENTION

A system improves identification of cardiac electrophysiological activities using cardiac signal (including surface ECG signals and intra-cardiac electrograms) energy mode and pattern identification and mapping to potential medical conditions. A system for heart performance characterization and abnormality detection comprises an interface for receiving an electrical signal indicating electrical activity of a patient heart over at least one heart beat cycle. A signal processor calculates a signal characteristic value comprising a summation of the square of values of amplitude of the electrical signal over at least a portion of a heart beat cycle. A comparator compares the calculated signal characteristic value with a threshold value to provide a comparison indicator. A patient monitor in response to the comparison indicator indicating the calculated signal characteristic value exceeds the threshold value, generates an alert message associated with the threshold.

DETAILED DESCRIPTION OF THE INVENTION

A cardiac arrhythmia analysis and event detection system employs excitation energy mode and energy consumption analysis of surface ECG signals and intra-cardiac electrograms for cardiac function diagnosis and characterization. The system identifies energy parameter patterns and maps derived parameter values to corresponding potential medical conditions and accurately determines a time stamp, as well as location and severity of cardiac pathology and clinical events. The system calculates a cardiac signal energy mode value, energy variation value and distributed energy value and identifies cardiac disorders, differentiates cardiac arrhythmias, characterizes pathological severity, predicts life-threatening events, and supports evaluation of administration of drugs. The system provides earlier prediction of clinical events, more detailed information on severity of the pathology and location of the abnormal function and tissue (such as muscle or heart chamber). The cardiac signal energy mode and distribution analysis is used to diagnose and quantify changes in cardiac tissue and cardiac excitation pathways, which typically shows changes earlier than cardiac electrophysiological signal waveform changes.

In one embodiment, cardiac signal energy distribution and energy consumption analysis is implemented in implantable cardiac devices and may be used for multi-channel cardiac electrophysiological signal diagnosis, such as for intra-cardiac signals from different leads of a multi-channel catheter or multiple catheters. Additionally cardiac signal energy mode calculation and diagnosis is used in combination with biological force or oximetric signal analysis, such as with hemodynamic pressure signals and SPO2 blood flow signals.

Early stages of CAD (coronary artery disease) are usually non-symptomatic and even invisible with current clinical cardiac signal analysis methods. The energy mode and distribution pattern analysis captures small changes indicating early stages of CAD, which reduces risk to cardiac patients. When certain abnormality or clinical events occur, cardiac tissue is affected earlier and a pacing excitation energy conducting mechanism is impacted. This results in abnormal variation in electrophysiological signal energy values, patterns, pacing and excitation power distribution enabling detection of cardiac arrhythmias. The system also performs electrophysiological signal energy cross balance and variation analysis as well as multi-channel or tissue site electrophysiological signal energy transition pattern analysis for circulation 2D and 3D function monitoring and mapping to potential medical conditions.

Figure 1:
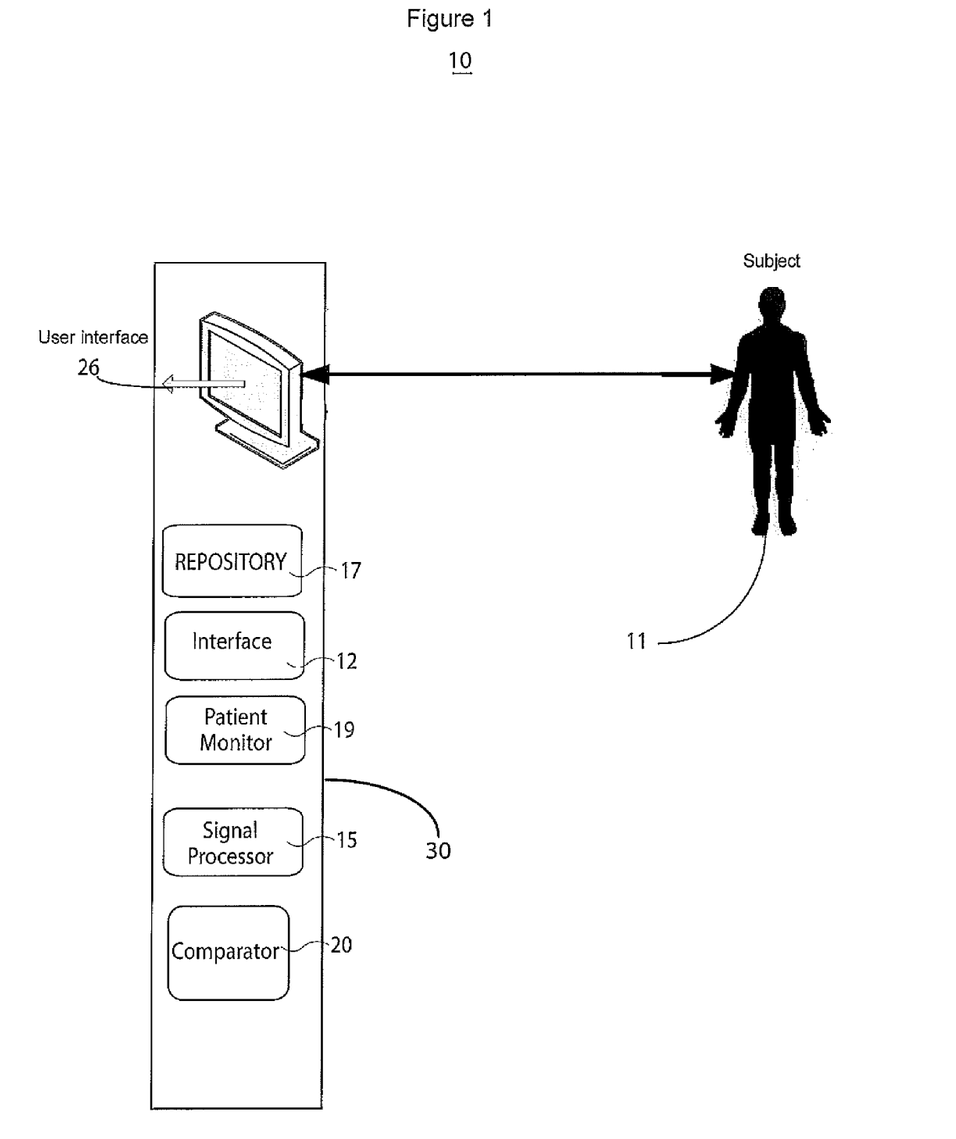
FIG. 1 shows a system for heart performance characterization and abnormality detection, according to invention principles.

FIG. 1 shows system 10 for heart performance characterization and abnormality detection. System 10 analyzes electrophysiological signals (including surface ECG, intra-cardiac electrograms, and heart activity signals, such as cardiac sound waveform) by deriving a signal characteristic value comprising a summation of the square of values of amplitude of an electrophysiological signal over at least a portion of a heart beat cycle. System 10 comprises at least one computer system, workstation, server or other processing device 30 including interface 12, repository 17, patient monitor 19, signal processor 15, comparator 20 and a user interface 26. Interface 12 receives an electrical signal indicating electrical activity of a heart of patient 11 over at least one heart beat cycle. Signal processor 15 calculates a signal characteristic value comprising a summation of the square of values of amplitude of the electrical signal over at least a portion of a heart beat cycle. Comparator 20 compares the calculated signal characteristic value with a threshold value to provide a comparison indicator. Patient monitor 19, in response to the comparison indicator indicating the calculated signal characteristic value exceeds the threshold value, generates an alert message associated with the threshold.

Figure 2:
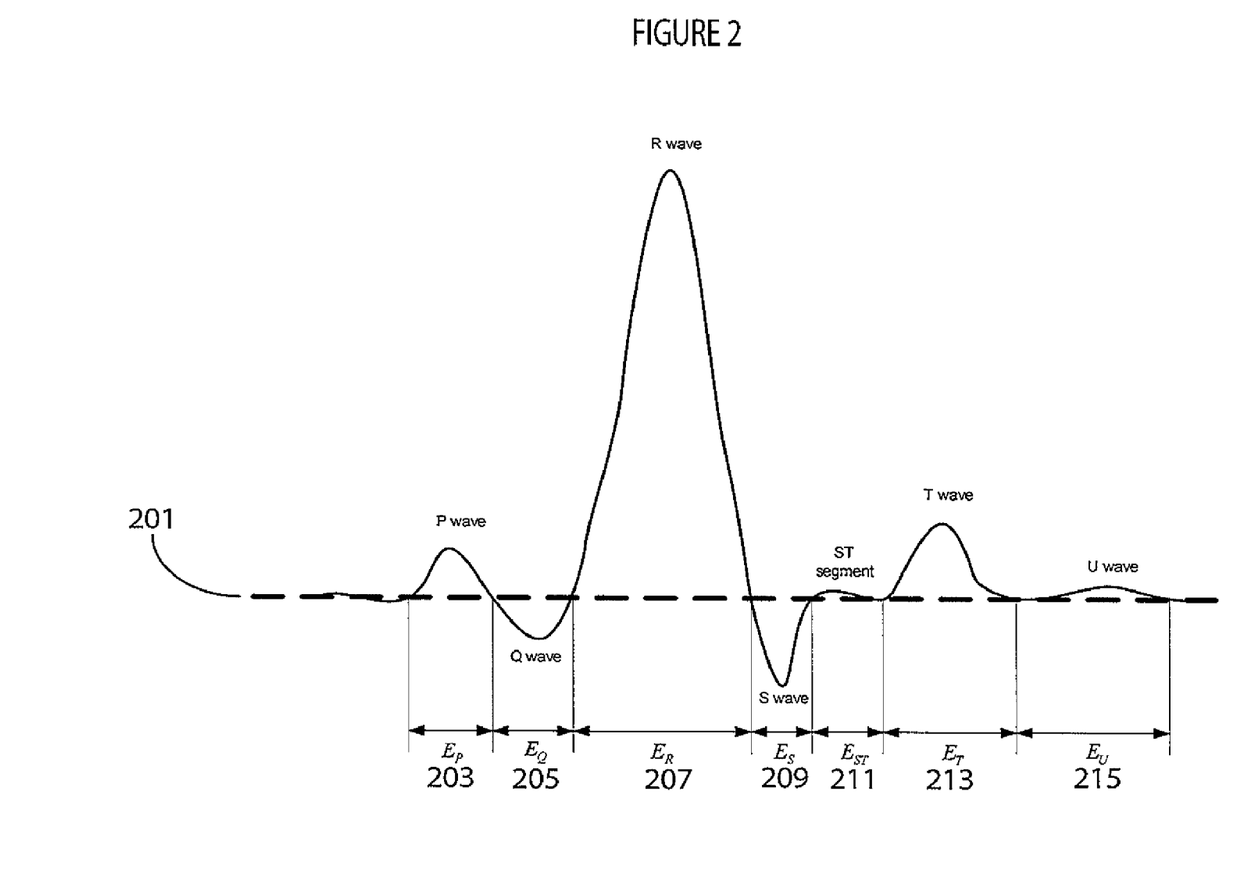
FIG. 2 illustrates different portions of a cardiac signal and associated electrophysiological functions.

FIG. 2 illustrates different portions of a cardiac signal and associated electrophysiological functions. System 10 (FIG. 1) segments an electrophysiological signal into portions used for energy distribution pattern and mode analysis. The different portions are associated with electrical activities of different tissue, muscle, heart chambers and functions such as repolarization and depolarization procedures. Furthermore, system 10 determines cardiac excitation and energy flow and a ratio of excitation conducting energy and energy consumption of heart tissue to diagnose and characterize signal changes and pathology severity and to predict clinical events. During a PTCA study and procedure, an ST segment portion is monitored and tracked to represent energy consumption and flow in heart chambers (for example, if there are some excitation blockages or muscle function slow-down, ST segment portion elevation occurs, which mean energy is accumulated in the ST segment portion).

A segmentation baseline (zero) 201 comprises a calibrated average voltage of a rest stage in the cardiac electrophysiological signal that is used to segment the signal into portions with the baseline crossing points identifying portion boundaries. The segmented portions comprise a P wave portion, a Q wave portion, an R wave portion, an S wave portion, and ST segment, a T wave portion and a U wave portion. Signal processor 15 (FIG. 1) calculates corresponding portion Energy parameter values, $E_P$ 203, $E_Q$ 205, $E_R$ 207, $E_S$ 209, $E_{ST}$ 211, $E_T$ 213, $E_U$ 215.

Signal processor 15 employs a calibrated baseline voltage in identifying different cardiac electrophysiological portions and calculates an energy parameter for individual portions as, $$E_{wave} = \int_{ROI\_wave} |A(t)|^2 \text{ or } E_{wave} = \sum_{i \in ROI\_wave} A(i)^2$$

where, $E_{wave}$ represents an energy integral value derived for a signal portion of interest, such as a P wave, ST segment, R wave, for example. A(•) is the magnitude (voltage amplitude in the application) of the data in the signal portion. The two equations are the continuous and corresponding discrete calculation methods, respectively. For example, $E_P$ is the integrated energy value of a P wave portion of a cardiac electrophysiological signal, which reflects heart atrial activity and energy consumption status. There are different clinical applications for the calculated consumption and conduction energy value. Signal processor 15 determines a pattern of values over a sequence of heart cycles and compares values with corresponding values obtained on a different occasion for the patient concerned or compares values of different sequential heart cycles. Processor 15 determines variation in energy values and performs statistical comparison of values obtained beat to beat to identify abnormality in atrial tissue and conduction pathways.

System 10 computes an energy value of portions of a cardiac electrophysiological signal acquired for myocardium and heart tissue to quantify heart energy consumption, flowing energy, energy ratio between chambers and real time energy consumption variation. Consumption, excitation energy flow and conduction energy of a whole heart are derived by comparing an energy integral value of positive and negative signal portions, which indicates a whole heart energy consumption. Specifically, heart_energy_consumption =

|ΣEnergy(positive_portion) − ΣEnergy(negative_portion)| heart_energy_consumption_ratio =

$$\frac{|\Sigma Energy(positive\_portion) - \Sigma Energy(negative\_portion)|}{|\Sigma Energy(positive\_portion) + \Sigma Energy(negative\_portion)|}$$

System 10 uses computed variation and variability of energy values of patient cardiac signals to identify and characterize cardiac abnormality and clinical events, especially in a cardiac energy pathway.

Depolarization and repolarization procedures are important cardiac functions. System 10 compares energy values and patterns of values over multiple heart cycles and mode of depolarization and repolarization, for example, by using a ratio. This enables a physician to readily track variation in either or both of the procedures, which may provide advance warning of ventricular tissue changes and abnormality caused by pathology (for example, myocardial ischemia). Specifically signal processor 15 calculates, $$\text{Repolarization\_Energy} = \sum_{i \in Repolarization} E_i, \text{ including } E_Q, E_R, E_S$$

$$\text{Depolarization\_Energy} = \sum_{j \in Depolarization} E_j, \text{ including } E_{ST}, E_T, E_U$$

$$\text{De\_Re\_polarization\_Energy\_ratio} = \frac{\sum_{j \in Depolarization} E_j}{\sum_{i \in Repolarization} E_i}$$

System 10 further uses calculated energy values and ratio of the depolarization and repolarization procedures to determine cardiac energy distribution and cardiac energy consumption patterns across a heart and maps derived values to corresponding medical conditions using predetermined mapping information. The predetermined mapping information associates ranges of the calculated energy values and ratio values with particular patient demographic characteristics and with corresponding medical conditions and system 10 uses patient demographic data including at least one of age weight, gender and height in comparing the calculated energy values and ratio values or values derived from the calculated energy values and ratio values with the ranges and generating an alert message indicating a potential medical condition. Furthermore, the relative changes of the energy between depolarization and repolarization is determined. A statistical evaluation and hypothesis test is applied to identify and adaptively change a threshold for change detection of the calculated energy related values to provide a threshold with a low failure rate of arrhythmia detection and false alarm generation.

System 10 calculates an index value that reflects absolute changes to quantify pathology related abnormality and distortions in a cardiac signal, tissue condition, signal conduction pathways and cardiac functions. System 10 uses energy calculation variability analysis to statistically quantify changes caused by clinical events and cardiac malfunctions (such as arthythmias) and minimizing noise effects associated with bio-noise and artifacts, such as respiration and electrical noise from other medical devices. System 10 employs different methods to reduce noise, including averaging calculated energy values of a particular portion over multiple heart cycles and averaging calculated energy variability values. System 10 calculates an energy variability value, $$\text{Energy\_EV} = \frac{|\text{MAX(Energy)} - \text{Min(Energy)}|}{\text{STD(Energy)}}$$

For example, in a real time digital data stream representing a cardiac electrophysiological signal, a window of N heart beats is employed and N energy calculations (such as energy value, energy ratio) are performed (hence there are a series of N values used), MAX and MIN is the maximum and minimum value of the N energy calculations, STD(Energy) is the standard deviation of the N value data series.

System 10 uses different methods for signal and data variability calculation including linear and non-linear functions. The system 10 variability calculation is not limited to the Energy_EV definition above and may employ different formats or equations indicating changes in a cardiac electrophysiological signal. The statistical analysis may also include high order statistical analysis (HOS), such as a bi-spectrum analysis. System 10 compares a calculated energy variability value against a threshold and generates an alert message in response to the value exceeding the threshold. System 10 employs a hypothesis test such as T test, $X^2$ test to improve detection confidence and reliably detect a clinical event and arrhythmia.

Figure 3:
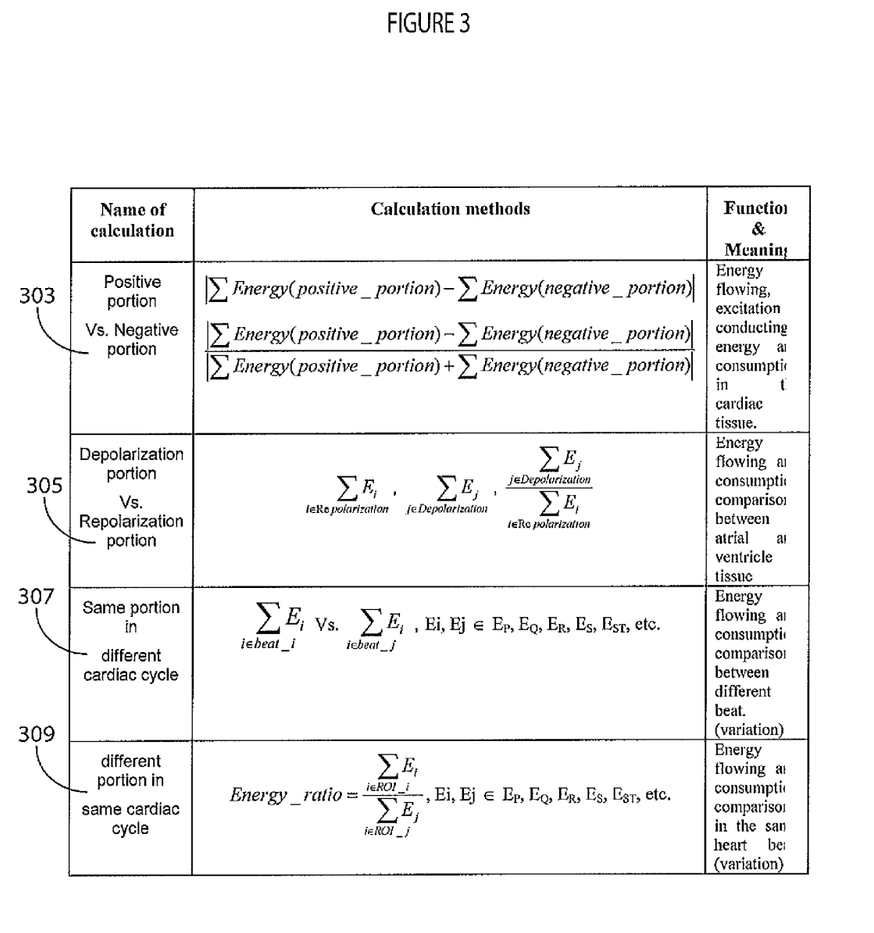
FIG. 3 shows a table summarizing energy pattern and mode calculations and corresponding clinical function indications, according to invention principles.

FIG. 3 shows a table summarizing energy pattern and mode calculations and corresponding clinical function indications employed by system 10. Row 303 shows system 10 calculations used to compare energy values calculated for positive and negative portions of a cardiac electrophysiological signal, respectively to indicate energy flow and energy consumption in cardiac tissue. Row 305 shows a system 10 calculation used to compare energy values calculated for depolarization and repolarization portions of a cardiac electrophysiological signal, respectively to indicate energy flow and energy consumption between atrial and ventricle tissue. Row 307 shows a system 10 calculation used to compare energy values calculated for a particular cardiac cycle portion in different heart cycles of a cardiac electrophysiological signal to indicate energy flow and energy consumption in the different heart cycles. Row 309 shows a system 10 calculation used to compare energy values calculated for different cardiac cycle portions in a single heart cycle of a cardiac electrophysiological signal to indicate energy flow and energy consumption in the single heart cycle.

Figure 4:
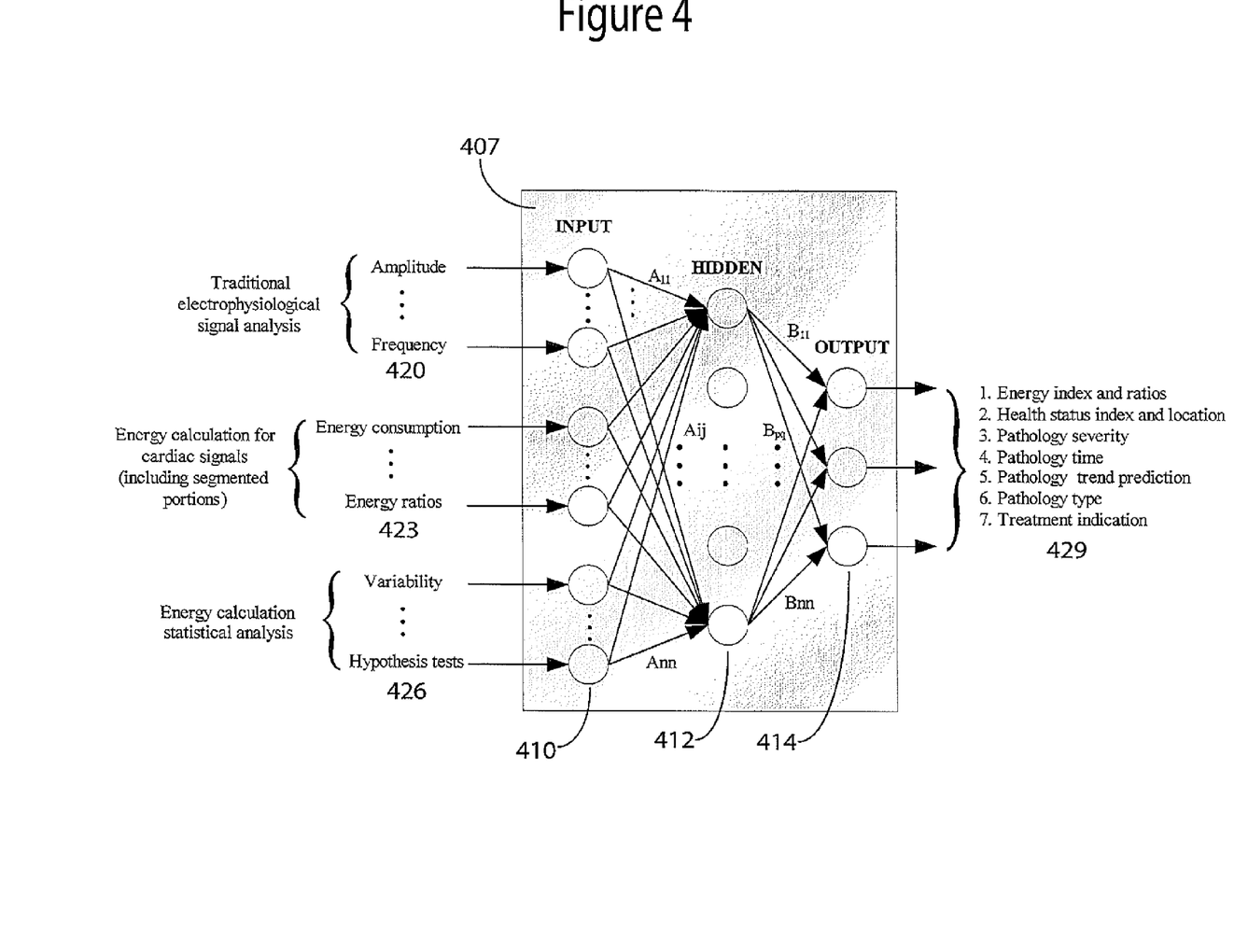
FIG. 4 shows an artificial neural network (ANN) used for heart performance characterization and abnormality detection, according to invention principles.

FIG. 4 shows an artificial neural network (ANN) system 407 used for heart performance characterization and abnormality detection. ANN unit 407 employs different energy pattern and mode analysis methods to identify cardiac disorders. ANN unit 407 maps one or more calculated energy related values 423, electrophysiological signal amplitude and frequency related parameters 420 and statistical values (energy variability and hypothesis test values) 426 derived from energy values, to output parameters 429. Output parameters 429 include an energy index value and ratio parameter, a patient health status index and location, a pathology severity indicator, a time of a cardiac event, a pathology trend indication, a pathology type indication and candidate treatment suggestions. ANN unit 407 structure comprises 3 layers, an input layer 410, hidden layer 412 and output layer 414. ANN unit $A_{ij}$ weights are applied between input layer 410 and hidden layer 412 components of the ANN computation and $B_{pq}$ weights are applied between hidden layer 412 and calculation index components 414 of the ANN computation. The $A_{ij}$ weights and $B_{pq}$ weights are adaptively adjusted and tuned using a training data set. ANN unit 407 incorporates a self-learning function that processes signals 420, 423 and 426 to increase the accuracy of calculated results.

ANN unit 407 maps input signals 420, 423 and 426 to a candidate diagnosis or treatment suggestion 429 to localize a tissue impairment within an organ and determine time of occurrence within a heart cycle. ANN unit 407 also identifies arrhythmia type (e.g., AF, MI, VT, VF), severity of arrhythmia treatment and urgency level and is usable for automatic heart condition detection, diagnosis, warning and treatment. Further unit 407 performs statistical analysis to construct a threshold used to detect tissue impairment and diagnose and predict cardiac arrhythmia and pathology.

Following a training phase with a training data set, ANN unit 407 maps signals 420, 423 and 426 to data 429 indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. The severity threshold of a pathology mapping decision may vary from person to person and is adjusted at the beginning of analysis. The system may be advantageously utilized in general patient monitoring and implantable cardiac devices for real time automatic analysis and detection of cardiac arrhythmias and abnormalities. ANN unit 407 is particularly useful in multi-channel signal energy mode and pattern analysis, for cross channel comparison and to further define arrhythmia type and location.

Figure 5:
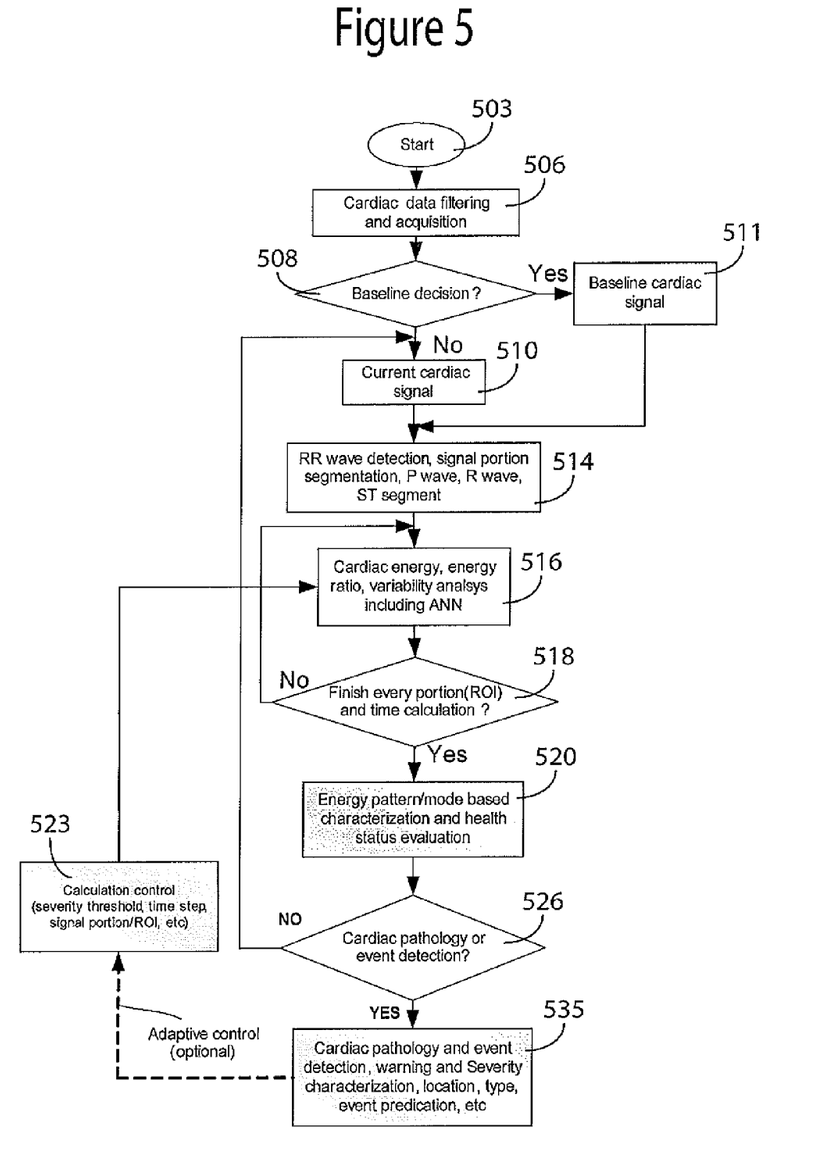
FIG. 5 shows a flowchart of a process for cardiac signal energy analysis, according to invention principles.

FIG. 5 shows a flowchart of a process for cardiac signal energy analysis performed by system 10. The system calculates energy values in different portions of a cardiac electrophysiological signal. The energy values represent energy flow and consumption and are used to derive an energy pattern, and variation as well as location, timing, severity and type of cardiac pathology and disease. Following the start at step 503, interface 12 in step 506 acquires digitized electrophysiological signals from multiple channels of a multi-channel intra-cardiac (e.g., basket) catheter indicating electrical activity at multiple cardiac tissue sites. Interface 12 filters the acquired electrophysiological signals using a filter adaptively selected in response to data indicating clinical application (e.g. ischemia detection, rhythm analysis application) and in step 508 determines whether a baseline level has already been determined for a current filtered signal 510. If a baseline level has not been selected, a baseline cardiac signal level is selected in step 511 by interface 12.

In step 514, signal processor 15 identifies different segments (QRS, ST, P wave, Q wave, R wave, S wave, ST segment, T wave, U wave segments, for example) of the filtered electrophysiological signals. In step 516, signal processor 15 calculates an energy value comprising a summation of the square of values of amplitude of a filtered electrophysiological signal over at least a portion of a heart beat cycle. Processor 15 performs a real time cardiac energy and variation calculation including a depolarization and repolarization energy ratio calculation. Processor 15 also calculates an energy ratio, and variability as previously described and in one embodiment, uses an ANN unit (e.g. ANN unit 407 FIG. 4). The calculations are iteratively performed in step 516 for different portions of a single heart cycle and for multiple heart cycles via step 518 until the desired signal portions are completed. Processor 15 in step 520 identifies a cardiac signal energy pattern comprising calculated energy values for each stage (portion) in a region of interest (ROI) of a heart cycle for a whole signal cycle and determines a health index.

In step 526 signal processor 15 employs mapping information, associating ranges of a calculated energy value or values derived from the energy value, with corresponding medical conditions (e.g., arrhythmias) in determining patient medical conditions, events and patient health status. If signal processor 15 and comparator 20 in step 526 determine a medical condition indicating cardiac impairment or another abnormality is identified, patient monitor 19 in step 535 generates an alert message identifying the medical condition and abnormality and communicates the message to a user. Processor 15 also determines the severity and location of the condition. Processor 15 in step 523 adaptively adjusts calculation time step, the selected portions and ROI of a filtered signal analyzed and adjusts a threshold employed by comparator 20 to improve medical condition detection. If signal processor 15 and comparator 20 in step 526 does not identify a medical condition, the process is repeated from step 510.

Figure 6:
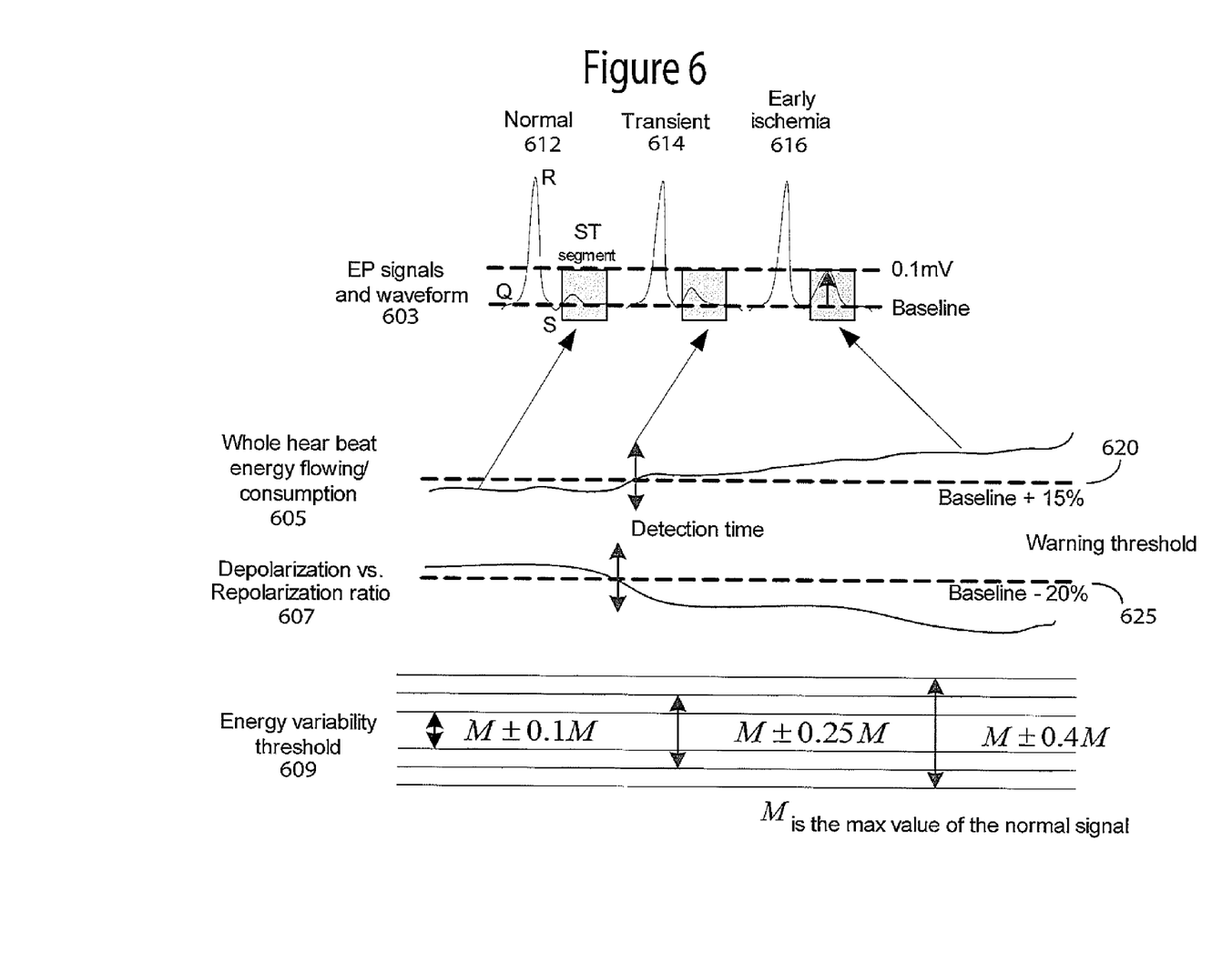
FIG. 6 shows energy pattern and mode ischemia analysis, tracking and characterization, according to invention principles.

FIG. 6 shows energy pattern and mode ischemia analysis, tracking and characterization and illustrates cardiac energy flow and consumption based detection of myocardial ischemia. System 10 (FIG. 1) performs an energy ratio and variability analysis by cardiac pattern quantification and characterization to identify different kinds of clinical events and cardiac pathologies, such as atrial fibrillation and ventricular tachycardia. The analysis includes single energy value calculation, (such as $E_P$, $E_R$) and a combined energy calculation for whole heart beat energy variability and depolarization-repolarization energy ratio calculation. An acute ischemia event and signal energy calculation is illustrated in FIG. 6 shows different episodes, including healthy (normal) 612, intermediate (transient) 614 and early ischemia 616 episodes. Detection of an EP signal amplitude (voltage) change for detection of a cardiac impairment, such as an ST segment (0.1 mV) change may take 20-30 minutes. In contrast, the system 10 signal energy mode analysis provides early detection and an index enabling a user to track myocardial function and perfusion procedure deviation which results from cardiac excitation force variation or myocardial muscle pathology.

The small transient ischemia episode 614 in electrophysiological signal 603 comprising an ST segment change (a trend) is detected and quantitatively characterized by using energy calculation and pattern analysis. The whole heart energy flow value is plotted in waveform 605 and the depolarization-repolarization ratio is shown in waveform 607 with accompanying detection variability thresholds 609. System 10 detects transient ischemia 614 in the energy flow waveform 605 using a threshold 620 set at waveform 603 baseline value plus 15% (with baseline energy normalized as 1). Additionally depolarization and repolarization ratio waveform 607 is calculated by system 10 to compare the energy distribution in the two procedures and to track ischemia tissue and arrhythmia location using a threshold 625 set at waveform 603 baseline value minus 20% (with baseline energy ratio normalized as 1). Thresholds 620 and 625 are adaptively and dynamically set in response to patient and signal quality characteristics (such as noise, artifact effect). For example, when the signal to noise ratio is 10:1, the threshold is set at 15% or more, while a threshold is set at 30% or more when the signal to noise ratio is 5:1 or less. The threshold is selected in response to sensitivity and stability of arrhythmia detection and quantification as indicated by a statistical analysis (such as a T test) to achieve a 95% confidence in detection of clinical events.

Figure 7:
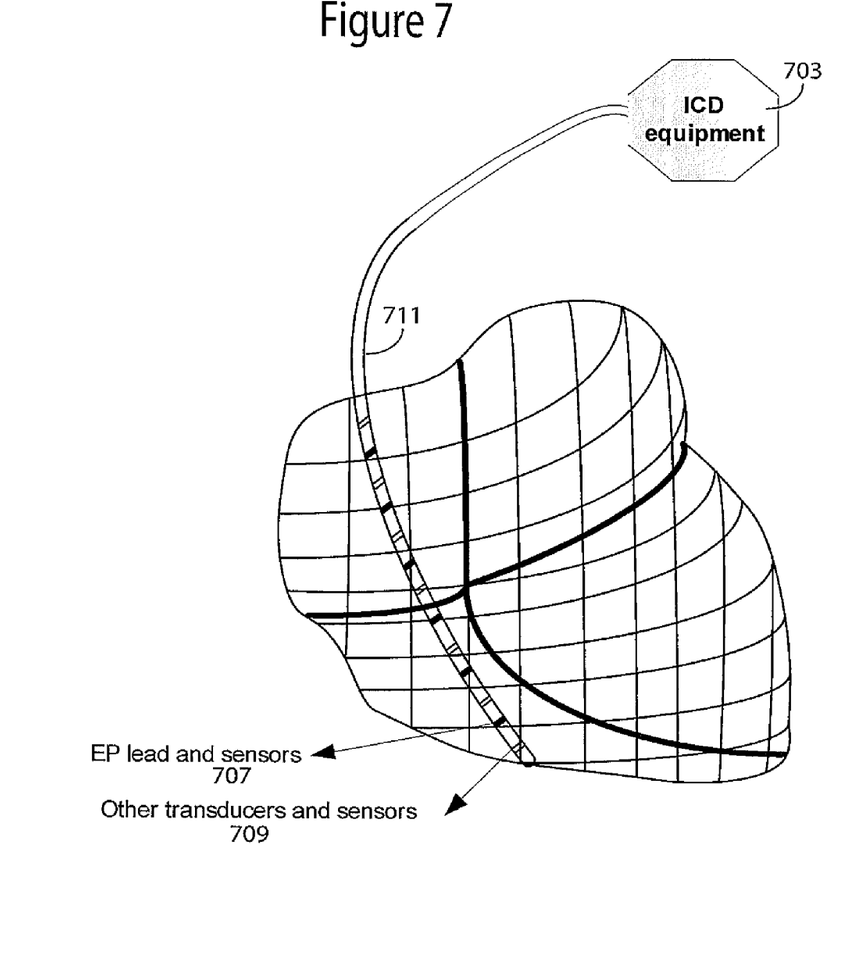
FIG. 7 shows an ICD (implantable cardioverter-defibrillator) system performing signal and waveform energy analysis, according to invention principles.

FIG. 7 shows an ICD (implantable cardioverter-defibrillator) system performing signal and waveform energy analysis. System 10 performs signal energy distribution analysis to characterize cardiac electrophysiological signal distortion and variation and determine cardiac excitation energy flow along a heart muscle pathway. ICD monitoring device 703 performs signal energy calculation and pattern analysis as well as intra-cardiac signal analysis. ICD device 703 is coupled to multi-channel sensors 707 and transducers 709 along catheter 711 providing real time signals, such as EP and pressure signals. Additionally, multi-channel signal energy calculations are performed to determine cardiac status and monitor cardiac functions in 2-dimension and 3-dimension heart mapping. Furthermore, multi-dimensional signal energy value mapping is used in real time for cardiac function diagnosis. System 10 (FIG. 1) uses multi-channel signal energy value mapping to visually indicate abnormal tissue location, potential abnormal pathways and arrhythmia severity to a user. The system calculates cardiac signal energy values for surface ECG signals, and other kinds of electrophysiological signals, such as ICEG signals (intra-cardiac electrograms) and hemodynamic pressure signals (such as IBP, NIBP signals, cardiac output signals). The cardiac signal energy analysis is employed in pacemaker and cardiac implantable devices for measurement and characterization of patient cardiac pathology and arrhythmia.

Figure 8:
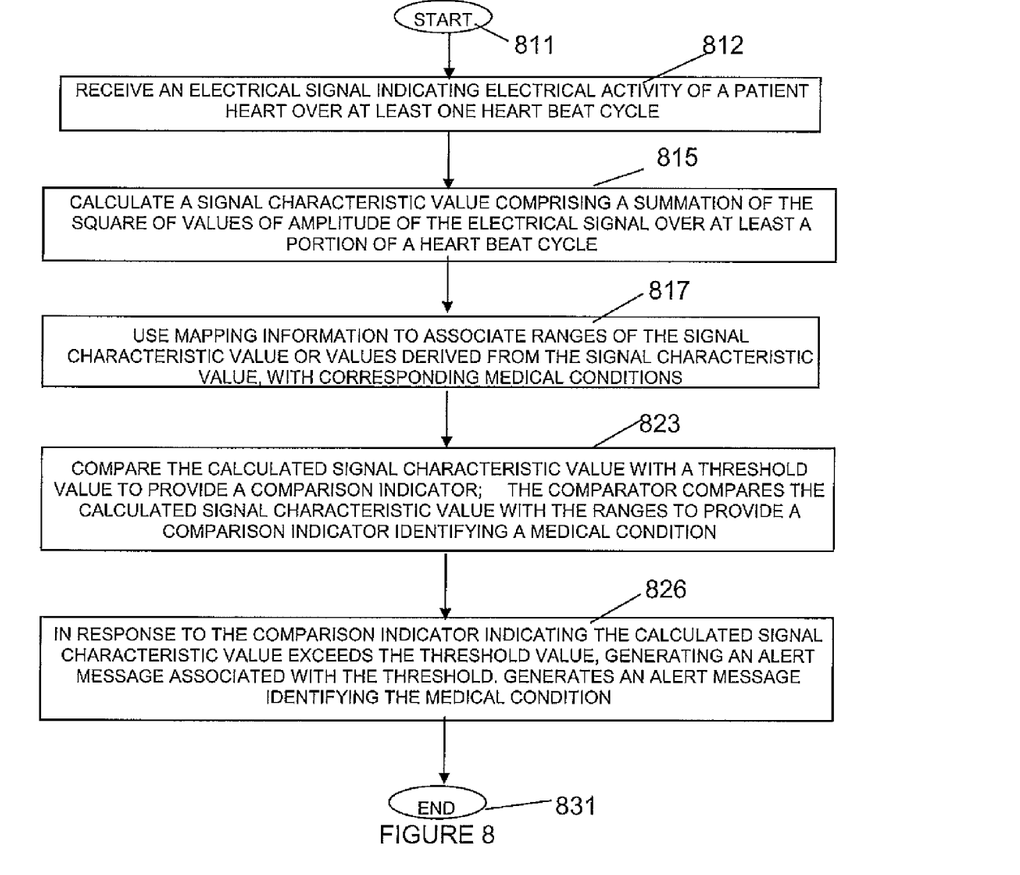
FIG. 8 shows a flowchart of a process used by a system for heart performance characterization and abnormality detection, according to invention principles.

FIG. 8 shows a flowchart of a process used by system 10 for heart performance characterization and abnormality detection. In step 812 following the start at step 811, interface 12 receives an electrical signal indicating electrical activity of a patient heart over at least one heart beat cycle and provides a digitized electrical signal. Signal processor 15 in step 815 calculates a signal characteristic value comprising a summation of the square of values of amplitude of the electrical signal (the digitized electrical signal) over at least a portion of a heart beat cycle. In one embodiment, signal processor 15 calculates a signal characteristic value as a function of a difference between, (a) a summation of the square of values of amplitude of said electrical signal over a positive portion of a heart beat cycle and (b) a summation of the square of values of amplitude of the electrical signal over a negative portion of a heart beat cycle. The summation of the square of values of amplitude of the electrical signal over at least a portion of a heart beat cycle comprises an integral of the square of amplitude values of the electrical signal over at least a portion of a heart beat cycle. In one embodiment, the summation of the square of values of amplitude of the electrical signal over at least a portion of a heart beat cycle comprises, $$E_{wave} = \sum_{i \in ROI\_wave} A(i)^2$$

Signal processor 15 calculates the signal characteristic value for a predetermined portion of a heart beat cycle in response to a synchronization signal and in one embodiment calculates the signal characteristic value as an averaged value over multiple heart beat cycles. The predetermined portion of the heart beat cycle includes an ST segment. Signal processor 15 also calculates signal characteristic values for a first and different second portion of a single heart cycle and calculates a ratio of the signal characteristic values for the first and different second portion of the single heart cycle. The first and different second portion of the single heart cycle correspond to repolarization and depolarization segments respectively. Further, signal processor 15 calculates signal characteristic values for the same portion of different first and second heart cycles and calculates a ratio of the signal characteristic values for the same portion of different first and second heart cycles.

In step 817 signal processor 15 uses predetermined mapping information in repository 17 associating ranges of the signal characteristic value or values derived from the signal characteristic value, with corresponding medical conditions. The predetermined mapping information associates ranges of the signal characteristic value with particular patient demographic characteristics and with corresponding medical conditions and the system uses patient demographic data including at least one of, age weight, gender and height in comparing the signal characteristic value or values derived from the signal characteristic value with the ranges and generating an alert message indicating a potential medical condition. Comparator 20 in step 823 compares the calculated signal characteristic value with a threshold value and with the ranges to provide a comparison indicator identifying a medical condition. The threshold value is derived from recorded electrical signal data for the patient or for a population of patients in which the population of patients has similar demographic characteristics including one or more of, (a) age, (b) weight, (c) gender and (d) height, to those of the patient. In one embodiment, signal processor 15 dynamically adjusts the threshold value in response to a determined sensitivity of arrhythmia detection.

In step 826, patient monitor 19, in response to the comparison indicator indicating the calculated signal characteristic value exceeds the threshold value or lies in a predetermined value range, generates an alert message associated with the threshold or the value range and identifying the medical condition. Patient monitor 19 substantially continuously monitors the comparison indicator for at least a 24 hour period. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system employs excitation energy value calculation and consumption analysis of cardiac activity signals for cardiac function diagnosis. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A system for heart performance characterization and abnormality detection, comprising: an interface for receiving an electrical signal indicating electrical activity of a patient heart over at least one heart beat cycle; a signal processor for calculating a signal characteristic value comprising a summation of the square of values of amplitude of said electrical signal relative to a zero voltage baseline of said electrical signal over at least a portion of a heart beat cycle; a comparator for comparing the calculated signal characteristic value with a threshold value to provide a comparison indicator; and a patient monitor for in response to said comparison indicator indicating the calculated signal characteristic value exceeds the threshold value, generating an alert message associated with the threshold.

2. A system according to claim 1, wherein
said signal processor calculates signal characteristic values for a positive portion of said electrical signal relative to said baseline and a negative portion of said electrical signal relative to said baseline, in a single heart cycle and
said patient monitor, in response to said comparison indicator indicating the calculated signal characteristic value lies in a predetermined value range, generates an alert message associated with the value range.

3. A system according to claim 2, wherein
said patient monitor substantially continuously monitors said comparison indicator for at least a 24 hour period.

4. A system according to claim 1, wherein
said baseline corresponds to a rest stage in a heart cycle and
said threshold value is derived from recorded electrical signal data for said patient.

5. A system according to claim 1, wherein
said threshold value is derived from recorded electrical signal data for a population of patients.

6. A system according to claim 5, wherein
said population of patients has similar demographic characteristics including at least two of, (a) age, (b) weight, (c) gender and (d) height, to those of said patient.

7. A system according to claim 1, wherein
said signal processor dynamically adjusts said threshold value in response to a determined sensitivity of arrhythmia detection.

8. A system according to claim 1, wherein
said signal processor calculates said signal characteristic value for a predetermined portion of a heart beat cycle in response to a synchronization signal.

9. A system according to claim 8, wherein
said predetermined portion of said heart beat cycle includes an ST segment.

10. A system according to claim 1, wherein
said signal processor calculates said signal characteristic value as an averaged value over a plurality of heart beat cycles.

11. A system according to claim 1, wherein
said signal processor calculates said signal characteristic value in response to a heart rate synchronization signal.

12. A system according to claim 1, including
a repository of mapping information, associating ranges of the signal characteristic value or values derived from the signal characteristic value, with corresponding medical conditions and
said comparator compares the calculated signal characteristic value with said ranges to provide a comparison indicator identifying a medical condition and
said patient monitor generates an alert message identifying said medical condition.

13. A system according to claim 12, wherein
said predetermined mapping information associates ranges of the signal characteristic value with particular patient demographic characteristics and with corresponding medical conditions and said system uses patient demographic data including at least one of, age weight, gender and height in comparing the signal characteristic value or values derived from the signal characteristic value with said ranges and generating an alert message indicating a potential medical condition.

14. A system according to claim 1, wherein
said interface provides a digitized electrical signal and
said signal processor calculates the signal characteristic value of the digitized electrical signal.

15. A system according to claim 1, wherein
said summation of the square of values of amplitude of said electrical signal over at least a portion of a heart beat cycle comprises an integral of the square of amplitude values of said electrical signal over at least a portion of a heart beat cycle.

16. A system according to claim 1, wherein
said summation of the square of values of amplitude of said electrical signal over at least a portion of a heart beat cycle comprises, $$E_{wave} = \sum_{i \in ROI\_wave} A(i)^2.$$

17. A system according to claim 1, wherein
said signal processor calculates signal characteristic values for a first and different second portion of a single heart cycle.

18. A system according to claim 17, wherein
said signal processor calculates a ratio of the signal characteristic values for the first and different second portion of the single heart cycle.

19. A system according to claim 17, wherein
the first and different second portion of the single heart cycle correspond to repolarization and depolarization segments respectively.

20. A system according to claim 1, wherein said signal processor calculates signal characteristic values for the same portion of different first and second heart cycles.

21. A system according to claim 20, wherein said signal processor calculates a ratio of the signal characteristic values for the same portion of different first and second heart cycles.

22. A system for heart performance characterization and abnormality detection, comprising: an interface for receiving an electrical signal indicating electrical activity of a patient heart over at least one heart beat cycle; a signal processor for calculating a signal characteristic value as a function of a difference between, (a) a summation of the square of values of amplitude of said electrical signal relative to a zero voltage baseline of said electrical signal over a positive portion of a heart beat cycle and (b) a summation of the square of values of amplitude of said electrical signal relative to said baseline over a negative portion of a heart beat cycle; a comparator for comparing the calculated signal characteristic value with a threshold value to provide a comparison indicator; and a patient monitor for in response to said comparison indicator indicating the calculated signal characteristic value exceeds the threshold value, generating an alert message associated with the threshold.

23. A system according to claim 22, wherein said signal characteristic value is calculated as a function of
a ratio of,
said signal characteristic value to
a sum of,
a summation of the square of values of amplitude of said electrical signal over a positive portion of a heart beat cycle and
a summation of the square of values of amplitude of said electrical signal over a negative portion of a heart beat cycle.

24. A method for heart performance characterization and abnormality detection, comprising the activities of: receiving an electrical signal indicating electrical activity of a patient heart over at least one heart beat cycle; calculating a signal characteristic value comprising a summation of the square of values of amplitude of said electrical signal relative to a substantially zero voltage baseline of said electrical signal over at least a portion of a heart beat cycle; comparing the calculated signal characteristic value with a threshold value to provide a comparison indicator; and in response to said comparison indicator indicating the calculated signal characteristic value exceeds the threshold value, generating an alert message associated with the threshold.

* * * * *